United States Patent [19]

Mapes et al.

[11] Patent Number: 4,904,583
[45] Date of Patent: Feb. 27, 1990

[54] CASCADE IMMUNOASSAY BY MULTIPLE BINDING REACTIONS

[75] Inventors: James P. Mapes, Raleigh; Randal A. Hoke, Cary, both of N.C.

[73] Assignee: Becton, Dickinson and Company, Franklin Lakes, N.J.

[21] Appl. No.: 53,896

[22] Filed: May 26, 1987

[51] Int. Cl.$^4$ .................. G01N 33/53; G01N 33/543; G01N 33/537; G01N 33/532
[52] U.S. Cl. ........................................ 435/7; 435/18; 435/19; 435/21; 435/23; 435/175; 435/181; 435/267; 435/810; 435/814; 436/505; 436/518; 436/537; 436/538; 436/540; 436/543; 436/544; 436/547; 436/800; 436/808; 436/817; 436/829
[58] Field of Search .................. 435/7, 18, 19, 21, 23, 435/175, 181, 267, 810, 814; 436/505, 518, 537, 538, 540, 543, 544, 547, 800, 808, 817, 821, 822, 829; 424/38

[56] References Cited

U.S. PATENT DOCUMENTS

| | | | |
|---|---|---|---|
| 4,463,090 | 7/1984 | Harris | 435/7 |
| 4,483,929 | 11/1984 | Szoka | 436/829 X |
| 4,543,325 | 9/1985 | Albert et al. | 435/7 |
| 4,595,655 | 6/1986 | Self | 435/7 |
| 4,649,105 | 3/1987 | Kasahara et al. | 436/518 |
| 4,703,017 | 10/1987 | Campbell et al. | 436/829 X |
| 4,746,631 | 5/1988 | Clogett | 436/518 |

FOREIGN PATENT DOCUMENTS 0181762  5/1986  European Pat. Off. .

*Primary Examiner*—Robert J. Warden
*Assistant Examiner*—Jack Spiegel
*Attorney, Agent, or Firm*—Richard E. Brown

[57] ABSTRACT

A method for enzyme immunoassay includes contacting under binding conditions a liquid suspected of containing an analyte, an antianalyte affixed to a solid support and a tracer having an enzyme conjugated thereto. A bound fraction is separated from the liquid and incubated in a second liquid with a masked ligand. The masked ligand is converted by the enzyme on the bound fraction to give free lignad which binds to an antiligand. A signal system, such as a signal enzyme and substrate therefor, or a label-loaded vesicle and vesicle lysing agent, is added to generate a signal used to detect or measure the analyte in the liquid. The invention includes a kit of materials useful in performing the assay of the invention.

31 Claims, 7 Drawing Sheets

CASCADE IMMUNOASSAY BY MULTIPLE BINDING REACTIONS

BACKGROUND OF THE INVENTION

1. Field of the Invention

This invention relates to immunoassay of an analyte and materials used therein, and more particularly relates to a method and materials for enzyme immunoassay which includes multiple binding reactions.

2. Background of the Invention

A variety of assay systems which are both rapid and sensitive has been developed to detect or determine the concentration of a substance, generally referred to as the analyte, in a liquid. Immunoassays depend on the binding of the analyte to a specific antianalyte, and have been particularly useful because they give high levels of specificity and sensitivity. These assays generally employ one of the above reagents in labeled form, the labeled reagent often being referred to as the tracer. Immunoassay procedures may be carried out in solution or on a solid support, and are of two basic types. In competitive assays, the tracer is labeled analyte, and the analyte and tracer compete for a limited number of antianalyte binding sites. In sandwich assays, the tracer is a labeled second antianalyte specific for a second determinant on the analyte giving an antianalyte-analyte-labeled antianalyte sandwich.

Various means for labeling have been developed. Radioimmunoassay (RIA) procedures use radioisotopes as labels, provide high levels of sensitivity and reproducibility, and are amenable to automation for rapid processing of large numbers of samples. However, all RIA procedures require a separation step, since the parameter measured (nuclear decay) cannot be controlled by changing assay conditions or components. In addition, isotopes are costly, have relatively short shelf lives, require expensive and complex equipment, and extensive safety measures for their handling and disposal must be followed.

Fluoroimmunoassay (FIA) uses fluorochromes as labels, provides direct detection of the label, and is readily adaptable to homogeneous assay procedures. However, known homogeneous FIA methods using organic fluorochromes, such as fluorescein or rhodamine derivatives, have not achieved the high sensitivity of RIA, largely because of light scattering by impurities suspended in the assay medium and by background fluorescence emission from other fluorescent materials present in the assay medium.

Enzymes have also been used as labels in immunoassay. Enzyme immunoassay (EIA) combines the advantages of RIA and FIA and overcomes many of the disadvantages of the other two methods. Enzyme labeled reagents are cheap to prepare and are highly stable thus giving a long shelf life, yet yield assays which approach the sensitivity of radioimmunoassay and which give objective results that can be determined either visually or with rather simple equipment, such as a spectrophotometer.

In conventional EIA, an enzyme is covalently conjugated with one component of a specifically binding antigen-antibody pair, and the resulting enzyme conjugate is reacted with a substrate to produce a color which is measured. Often, an unconjugated component is immobilized on a solid support. Representative of such conventional EIA is U.S. Pat. No. 3,654,090 to Schuurs et al.

Analytes to be determined in biological fluids are often present in the range of $10^{-9}$ to $10^{-12}$M, and conventional EIA techniques may not be sufficiently sensitive to detect analytes present in such low concentrations. In the art, EIA sensitivity has been increased by cascade amplification in which the number of detectable (generally colored) molecules is increased by use of multiple enzymes or enzyme derivatives. In this procedure, a first enzyme conjugated to an assay component may activate a second enzyme or enzyme derivative which catalyzes a color producing reaction or formation of a third enzyme. Exemplary of this technique is U.S. Pat. No. 4,463,090 to Harris.

U.S. Pat. No. 4,446,231 to Self discloses a cycling amplification enzyme immunoassay which includes primary and secondary enzyme systems and a modulator for the second enzyme system. The primary system includes a first enzyme coupled to a ligand. In a first embodiment of the Self invention, the first enzyme system acts on a modulator precursor to liberate a modulator. The modulator is a cofactor of the secondary enzyme which activates the second enzyme system to catalyze the reaction of a substrate to a detectable product. During the reaction, the modulator is converted to an inactive form, and cycling is accomplished by a third enzyme which reactivates the modulator. In a second embodiment, the modulator is an inhibitor of the secondary system and is removed by the primary enzyme system whereby the secondary system is activated to act on the substrate and thereby produce the detectable product.

A homogenous competitive EIA in which an analyte-cytolysin conjugate binds competitively to a specific antianalyte is disclosed by Freytag et al. in U.S. Pat. No. 4,517,303. The cytolysin component of unbound conjugate ruptures vesicles containing a sequestered marker.

U.S. Pat. No. 4,543,325 to Albert et al. discloses a method for immunoassay of creatinine. 1-Methylhydantoin formed enzymatically in the assay fluid competes with enzyme-labeled 1-methylhydantoin for a limited quantity of anti-1-methylhydantoin antibody on a solid phase.

SUMMARY OF THE INVENTION

A method for immunoassay of an analyte in a liquid includes signal amplification by a plurality of binding reactions carried out by any conventional sandwich, competition or saturation technique. The analyte binds to an antianalyte and a ligand binds to an antiligand. A signal system detects ligand and relates its concentration to that of the analyte. In one configuration of the assay, both the antianalyte and antiligand are affixed to a solid support, and the analyte binds to both the antianalyte and a tracer to form a sandwich on the support. The tracer includes an enzyme (hereinafter referred to as the unmasking enzyme) which converts a masked ligand conjugated to a second enzyme (hereinafter referred to as the signal enzyme) to enzyme-conjugated free ligand which binds to antiligand on the support. The signal enzyme thereby bound to the support converts an enzyme substrate to a product which provides a measurable signal.

In another assay configuration, the signal system includes a label-loaded vesicle. The free ligand liberated from the masked ligand competes, preferably in homogeneous mode, with ligand conjugated to a vesicle for binding sites on antiligand in a fluid phase of the assay. Vesicles which thereby have ligand bound to antiligand on their surfaces are lysed to release a label encapsulated in the vesicles. The label provides a measurable signal which is proportional to the concentration of the analyte in the liquid.

In a semihomogeneous double competition vesicle-based assay configuration, the enzyme-labeled tracer competes with the analyte for a limited number of support-affixed antianalyte binding sites.

Preferred ligands are relatively small molecules for which specific antiligands are readily available and for which masked modifications which do not bind the antiligand can be readily prepared. Vitamins, antibiotics, drugs and the like in which a functional group has been phosphorylated, esterified or amidated are suitable masked ligands. Since the unmasking enzyme component of the tracer converts the masked ligand to ligand, suitable enzymes may be cyclases, isomerases, and preferably hydrolases such as phosphatases, esterases and peptidases.

The signal enzyme, substrate and product may comprise any detection system conventional in the EIA art.

The assay method of the present invention provides increased sensitivity of 100 fold or more in the determination of analytes present in biological fluids in very low concentration. For assays not requiring high sensitivity, this increased sensitivity can be utilized to decrease assay time. The improved sensitivity achieved by the multiple binding reactions of the present invention represents a significant improvement over known immunoassay methods.

DETAILED DESCRIPTION OF THE INVENTION

Figure 1:
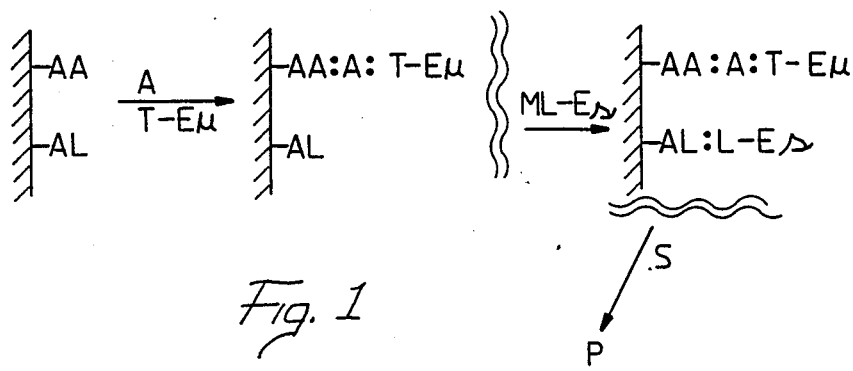
FIG. 1 is a flow sheet depicting a sandwich saturation configuration for the assay method of the invention.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

A method for immunoassay of an analyte provides enhanced sensitivity by signal amplification based on multiple binding reactions using a plurality of binding components. In accordance with the method, a substance, hereinafter referred to as the analyte, suspected of being present in a liquid may be determined when present in the liquid in very low concentration. In this disclosure, the term "determined" is understood to mean detection of the analyte or measurement of its concentration.

The method of the invention includes two or more reactions. By the term "binding reaction," as used herein, is meant a specific binding reaction of an antigen and an antibody, a hapten and an antibody, two antibodies, or any appropriate analogue of an antigen, an antibody, or a hapten which also binds specifically.

The first binding reaction may be carried out in any suitable liquid. For example, the liquid may be a body fluid suspected of containing the analyte, such as serum, urine, cerebrospinal fluid, pleural fluid or the like. Alternatively, the liquid may be water, saline or any appropriate buffer, or a mixture of body fluids and other liquids to which has been added a sample suspected of containing ligand. After a separation step, the second and any subsequent binding reactions preferably are carried out in water, saline or a buffer.

One or more incubation steps may be included in the method to induce binding. Incubation may be carried out at any temperature and for any length of time suitable to facilitate binding, preferably from about 20° to 40° for about one minute to four hours. Antianalyte, analyte and tracer which are bound and ligand and antiligand which are bound are hereinafter referred to as bound fractions and assay components which do not bind are hereinafter referred to as the free fraction. The assay may, but need not, be carried out in such a way that equilibrium is established between the bound and free fractions.

The preferred assay method includes at least one separation step. Any conventional method, such as filtration, decantation, centrifugation, aspiration and the like, may be used to separate the bound fraction from the free fraction in the liquid phase of the assay mixture. When a binding reaction has been carried out on a solid support, as described below, the liquid phase is conveniently decanted, the solid support washed to ensure removal of the free fraction and any other materials which would interfere with the assay, resuspended in a suitable liquid hereinafter referred to as the second liquid, such as water, saline or buffer prior to adding the assay components for the second binding reaction.

It is preferred, but not essential, that one or more of the assay components be attached to the surface of a solid support. As known in the art, the solid support may be any support which does not substantially interfere with the assay. Exemplary of solid supports which may be used are glass and polymeric materials, such as polyethylene, polystyrene and the like. Such supports may be fabricated into any suitable shape, such as sheets, tubes, wells, or preferably, plates such as microtiter plates. For example, an assay component, preferably the antianalyte (described below), may be attached to the inside walls and bottom of a tube, preferably a plastic tube with one closed end, or most preferably, to the wells of a microtiter plate.

Subsequent to attachment of the assay components to the solid support, any remaining binding sites on the support are preferably filled with an inert protein, such as, for example, albumin.

Any of the conventional techniques well known in the immunoassay art, such as competitive, sandwich and saturation procedures may be used for the binding reactions of the invention. In FIGS. 1–7, representative nonlimiting assay configuration are described wherein the following definitions apply:

| | |
|---|---|
| AA | antianalyte |
| AL | antiligand |
| A | analyte |
| T | tracer |
| Eu | unmasking enzyme |
| Es | signal enzyme |
| M | masking group |
| L | ligand |
| ML | masked ligand |
| S | substrate |
| P | product which generates a measureable signal |
| ⌐ | solid phase |
| ⋂ | separation step |
| — | chemical or physical conjugation |
| : | immunological binding |
| ○ | sac, vesicle, liposome or the like |
| La | label |
| C | complement |

A sandwich saturation assay configuration is shown FIG. 1. A solid support having affixed thereto an antiligand and an antianalyte is contacted with a liquid suspected of containing an analyte and with a tracer comprising a second antianalyte conjugated to an unmasking enzyme to give an antianalyte:analyte:tracer sandwich on the support. After a separation step, the support is contacted with a masked ligand conjugated to a signal enzyme. The unmasking enzyme converts the masked ligand to free ligand conjugated to signal enzyme, which binds to the antiligand on the support. After a second separation step, there is added a substrate which is converted by the signal enzyme on the support to a product which provides a measurable signal.

Figure 2:
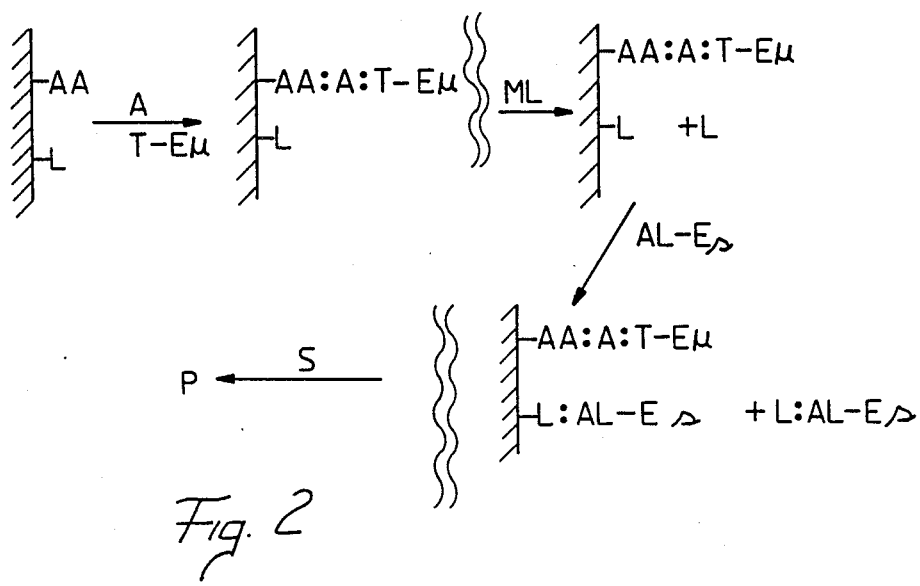
FIG. 2 is flow sheet of a sandwich-competition configuration for the assay method of the invention.

A sandwich-competition assay configuration is shown in FIG. 2. A solid support having affixed thereto antianalyte and ligand is contacted under binding conditions with analyte and a tracer consisting of a second antianalyte conjugated to an unmasking enzyme to give a sandwich on the support. After separation, there is added a masked ligand which reacts with the unmasking enzyme to give free ligand. A limited quantity of antiligand conjugated to signal enzyme is added. Free ligand and the support bound ligand compete for the limited number of antiligand binding sites giving a mixture of supported and unsupported bound fractions containing signal enzyme. After the unsupported bound fraction is removed by a second separation step, substrate is added and converted by the signal enzyme component of the supported bound fraction to product which provides a measurable signal.

Figure 3:
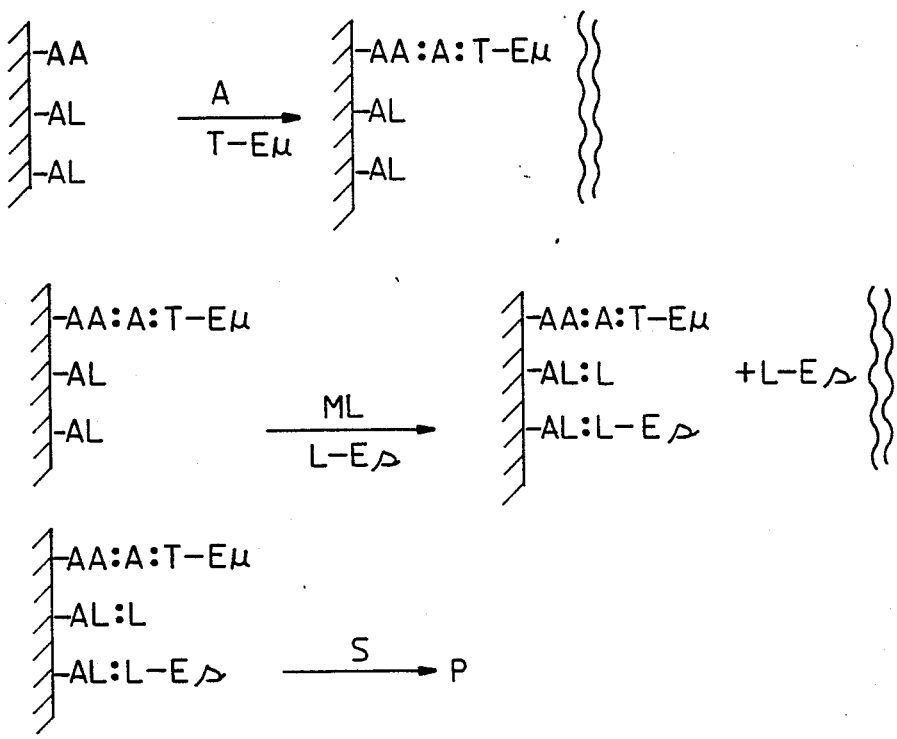
FIG. 3 is a flow sheet of a sandwich-competition assay configuration similar to that of FIG. 2.

The method depicted in FIG. 3 is also a sandwich-competition configuration which differs from that of FIG. 2 in reversing the roles of the ligand and antiligand. It is seen that, in FIG. 3, the antiligand is affixed to the support and the ligand is conjugated to the signal enzyme.

Figure 4:
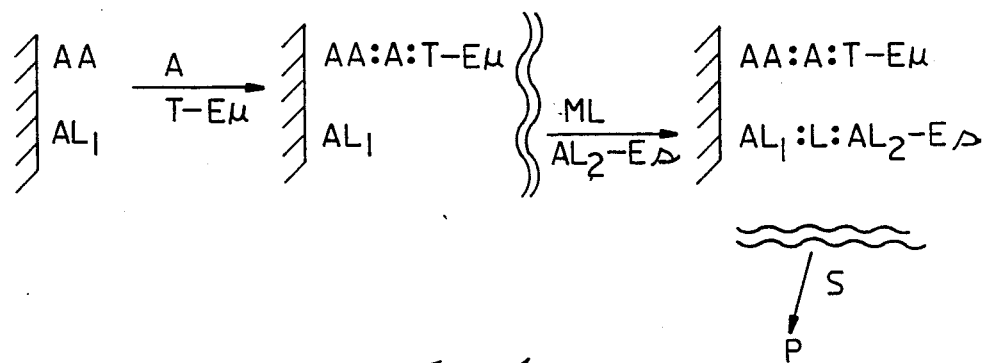
FIG. 4 is a flow sheet of a double sandwich configuration for the assay method of the invention.

FIG. 4 illustrates a double sandwich assay configuration utilizing a polyvalent ligand. A solid support having affixed antianalyte and a first antiligand is contacted with analyte and a tracer consisting of a second antianalyte conjugated to an unmasking enzyme to give a sandwich on the support. After separation, a masked ligand and a second antiligand conjugated to signal enzyme are added. Unmasking gives free ligand which binds to the first and second antiligands to give a second sandwich as the support. After separation, substrate for the signal enzyme is added and converted to a product providing a measurable signal.

Figure 5:
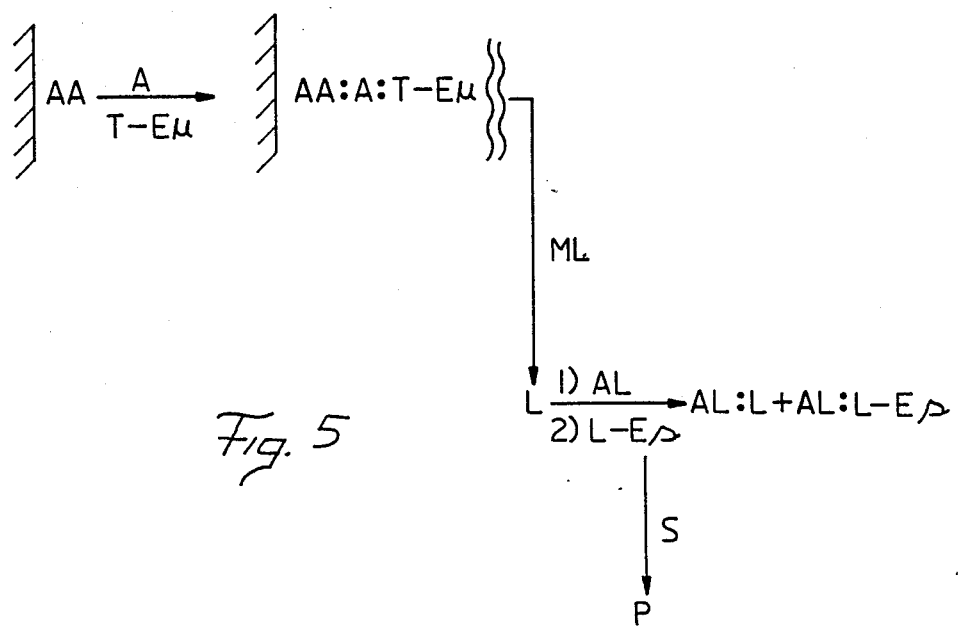
FIG. 5 is a flow sheet of a semihomogeneous sandwich-competition configuration for the assay method of the invention.

The assay of the invention may be carried out in a semihomogeneous format. In FIG. 5, an antianalyte:analyte:tracer sandwich is prepared on the solid support, and after separation, is contacted with the masked ligand, ligand conjugated to the signal enzyme and antiligand. Free ligand liberated from the masked ligand by the unmasking enzyme component of the tracer competes with the ligand conjugated to signal enzyme for antiligand binding sites. The activity of the signal enzyme conjugated to ligand bound to antiligand is sterically inhibited by the binding, so that, on adding substrate, product is formed predominantly from unbound ligand-signal enzyme conjugate. This allows the signal to be measured without a second separation step.

Figure 6:
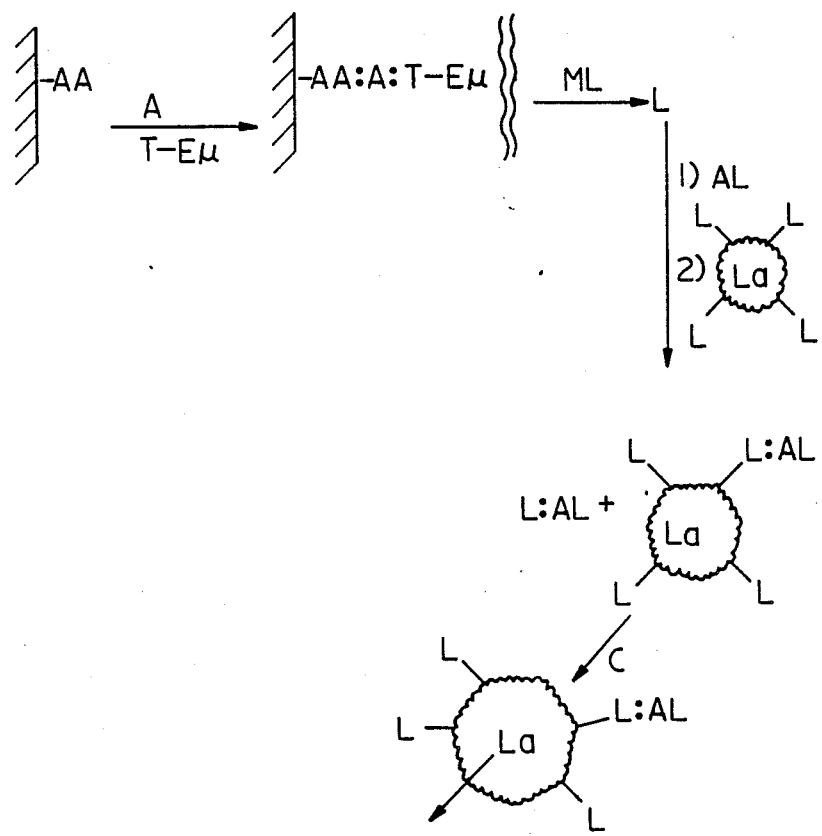
FIG. 6 is a flow sheet depicting a semi-homogeneous liposome-based sandwich-competition configuration for the assay method of the invention.

FIG. 6 shows a solid support having affixed thereto sufficient antianalyte to bind substantially all of an analyte suspected to be present in a liquid. The support is contacted under binding conditions with a tracer consisting of a second antianalyte conjugated to an unmasking enzyme to give an antianalyte:analyte:tracer sandwich on the support. After a separation step, a masked ligand is added and converted by the unmasking enzyme to give free ligand. A limited quantity of an antiligand and a vesicle having a label encapsulated therein and the ligand conjugated to the surface thereof are added. The free ligand and the vesicle-conjugated ligand compete for antiligand binding sites giving a mixture of antiligand bound to free ligand and antiligand bound to vesicle-conjugated ligand. A vesicle lysing agent, preferably complement, is added and those vesicles having bound ligand:antiligand on their surfaces are thereby lysed to release the label. The label may be part of any conventional detection system, as, for example, a dye or a signal enzyme as described below. In this assay configuration, the quantity of label released is inversely proportional to analyte concentration in the liquid.

Figure 7:
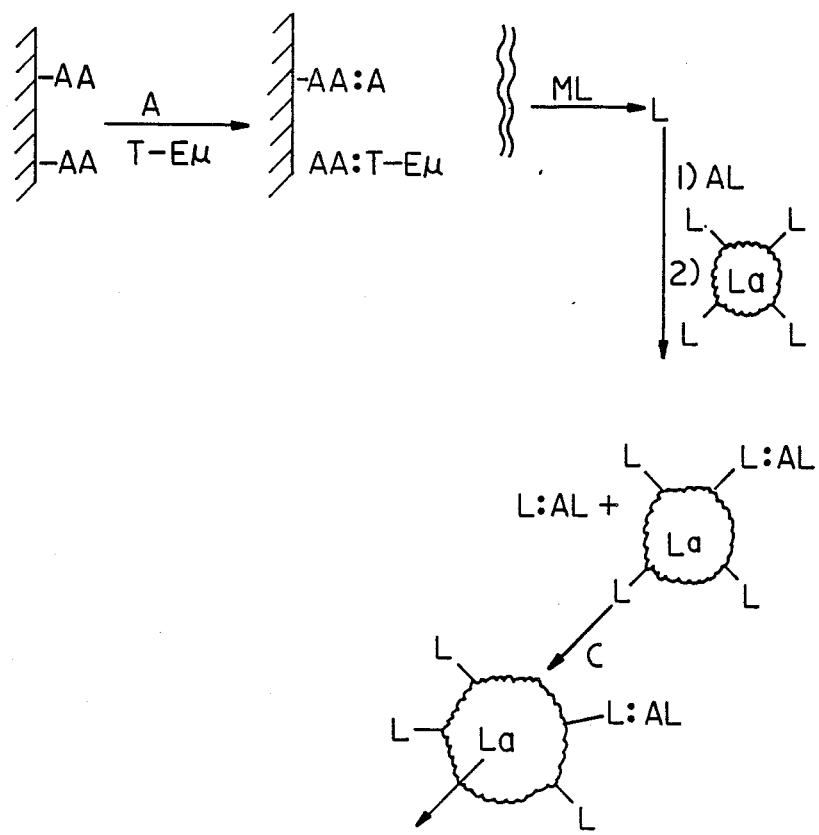
FIG. 7 is a flow sheet of a liposome-based double competition configuration of the assay method of the invention.

FIG. 7 illustrates a semihomogeneous vesicle based double competition assay format. In this configuration, the tracer is analyte conjugated to the unmasking enzyme. Competition takes place between analyte and tracer for a limited quantity of antianalyte on the support. After a separation step, masked ligand is added and converted by the unmasking enzyme on the support to give free ligand. The assay is then completed as described above by adding a limited quantity of antiligand and ligand-conjugated vesicles, the label being released by lysis of vesicles having bound ligand-antiligand thereon. In this assay configuration, the quantity of released label is directly proportional to analyte concentration.

As is evident to one skilled in the art, the assay components and steps of FIGS. 1–7 may be modified to provide a wide variety of other assay configurations, and the invention is contemplated to include all assay configurations which provide signal amplification achieved with multiple binding reactions.

Having now described in general terms representative assay configurations of the invention, a detailed description of the assay components will be given. The analyte may be from any source, and may be an antigen, an antibody or a hapten. For example, the analyte may be an antigen present in a body fluid, or it may be isolated from a body fluid and subsequently introduced into a different liquid, such as buffer. In other cases, the analyte may be from a source other than a body fluid, as, for example, a culture of microorganisms or a cellular extract thereof. Preferred analytes are antigens, most preferably viral antigens present in a body fluid, such as Herpes simplex virus (HSV), Adenovirus, Influenza A virus, Parainfluenza 3 virus and Respiratory syncytial virus.

The antianalyte may be an antigen or an antibody, either monoclonal or polyclonal, or it may be any appropriate analogue thereof which reacts specifically with the analyte. The preferred antianalyte is an antibody specific for an antigen analyte. The antianalyte may also be an antibody complex consisting of a plurality of bound antibodies, as, for example, a second antibody bound specifically to a first antibody, or it may be an ensemble of polyclonal antibodies or a mixture of several monoclonal antibody molecules which bind simultaneously to different surface areas of the analyte. Generally, the second antibody is raised against the first antibody in a different species. The plurality of bound antibodies in the complex may contain from about two to ten or more antibodies.

With respect to the quantity of antianalyte, it is preferred, in a sandwich step, to use excess antianalyte so that sufficient binding sites are available to bind essentially all of the analyte, and, in a competition step, to use a limited quantity of antianalyte.

The tracer comprises two components, the unmasking enzyme conjugated to the antianalyte (sandwich mode) or to the analyte (competition mode). The unmasking enzyme converts the masked ligand, which does not bind to antiligand, to free ligand which does bind. The conversion of masked ligand to free ligand by the unmasking enzyme may be, for example, cleavage of a functional group, cyclization of an acyclic compound, opening of a ring, isomerization, and the like. A suitable unmasking enzyme is, for example, a cyclase, such as adenylate cyclase, an isomerase, such as delta 5-3-ketosteroid isomerase, and, preferably, a hydrolase such as a protease, an esterase and a phosphatase. Preferred hydrolases are alkaline phosphatase, trypsin, $\beta$-lactamase, creatinine iminohydrolase and carboxyesterase.

It is understood that the unmasking enzyme merely represents the preferred catalyst for the conversion of the masked ligand to the free ligand, and the invention is contemplated to include any catalyst which can perform this conversion. Thus, suitable catalysts include proteins, such as enzymes and cofactors, and non proteins, such as inorganic compounds and hem-porphyrin systems.

The ligand may be any substance to which a specific antiligand may be developed and which may be supplied in masked form. Preferred ligands are molecules, preferably organic, of relatively low molecular weight generally less than 2000 and preferably between 200 and 1000. Suitable ligands are, for example, steroids, hormones, vitamins, drugs, coenzymes and the like, as exemplified by the ligand entries in Charts I and II below.

Although the preferred ligands are low molecular weight organic molecules, the invention is contemplated to include other ligands of higher molecular weight. For example, it is understood by those skilled in the art that the preferred ligand for the configuration of FIG. 3 has a plurality of binding sites, as, for example, a protein.

The antiligand which binds specifically to the ligand is preferably a protein, such as avidin, a lectin, an active enzyme, or, most preferably, an antibody raised against the ligand by conventional methodology. Examples of preferred ligands and their specifically binding antiligands are given in Chart I.

| CHART I | |
|---|---|
| LIGAND | ANTILIGAND |
| Folate | Folate binding protein |
| Thyroxin | Thyroxin binding globulin (TBG) |
| Vit $B_{12}$ | Intrinsic Factor |
| Riboflavin | Riboflaving binding protein |
| Steroid | Steroid binding proteins |
| Pepstatin | Pepsin |
| Cyclic adenosine monophosphate (C-AMP) | C-AMP dependent protein kinase |
| Biotin | Avidin |
| Fluorescein | Antifluorescein antibody |

As mentioned above, the masking component of the masked liquid prevents the ligand from binding to the antiligand until the masked ligand is modified by the unmasking enzyme. As such, the masking group may be a chemical group conjugated to the ligand and cleaved by the unmasking enyzme. The masked ligand may additionally be a functionally modified ligand, for example, it may be a double bond isomer of the ligand, such as a data 5-3-ketosteroid, which must be isomerized to the delta 4 isomer prior to binding. It may also be a cyclic form, such as a $\beta$-lactam antibiotic, of an acyclic ligand, or conversely it may be an acyclic form (adenosine monophosphate) of a cyclic ligand (cyclic AMP).

It is evident that the choice of masked ligand depends on the unmasking enzyme employed. If the enzyme is a phosphatase, a masking group such as a phosphate group may be used wherein the masked ligand may be a steroid phosphate, as, for example, 3-phosphoestrone. If the enzyme is an esterase, a masking group such as an acetyl group may be used wherein the masked ligand may be 3-acetoxyestrone. Representative nonlimiting examples of suitable unmasking enzyme-masked ligand-ligand combinations are given in Chart II below:

| CHART II | | |
|---|---|---|
| ENZYME | MASKED LIGAND | LIGAND |
| Alkaline phosphatase | 3-phosphoestrone | estrone |
| 3-Keto-delta 5 steroid isomerase | Delta 5-androstene-dione | Delta 4-androstene-dione |
| Adenylate cyclase | ATP | Cyclic AMP |
| Beta-Lactamase | Beta-Lactam antibiotics | Open ring lactams |
| Creatinine-iminohydrolase | Creatinine | 1-Methylhydantoin |
| trypsin | peptide | smaller peptide |
| carboxy esterase | fluorescein butyrate | fluorescein |

Suitable other combinations of unmasking enzyme, masked ligand, free ligand and antiligand to be used in accordance with the method of the invention are readily evident to those skilled in the art and no further details with respect to this aspect of the invention are needed.

Liberation of free ligand from the masked ligand by the unmasking enzyme results in the second binding reaction and triggers a signal system by which the analyte is determined. Signal systems for EIA are well-known to those skilled in the art, and the invention is contemplated to include any conventional system. For example, as shown in FIGS. 1–4, the system may include a signal enzyme conjugated to either the ligand or the antiligand. The signal enzyme converts a substrate for the enzyme to a detectable product. Such systems are described in detail by Miyai, "Advances in Nonisotopic Immunoassay," Advances in Clinical Chemistry, vol. 24, H.E. Spiegel, ed., Academic Press, Inc. (1975), 61, and no further details are necessary for a complete understanding of this aspect of the invention.

When the signal provided by the product is enzymatically generated, it is generally associated with color. A color may develop as product forms, or the product may be colorless and the signal may be disappearance of color or a change from one color to another. Alternatively, the signal may be a change in the rate at which the substrate is converted to the product, for example, the color of a substrate may be observed to remain unchanged for a specified length of time. Thus, measurements of the signal may be made under either kinetic or thermodynamic conditions. Kinetic measurements determine the rate of change which occurs over a period of time, and are generally carried out by making a series of measurements at various times after combining the assay reagents. Thermodynamic measurements determine the extent of change which has occurred when equilibrium has been reached between the substrate and the product of the indicator reaction. Measurements may be made either instrumentally or, preferably, with the naked eye.

An alternative signal system is illustrated in FIGS. 6 and 7 and includes a sac, vesicle, or preferably a liposome, having a label encapsulated therein and ligand conjugated to the surface thereof. In this embodiment of the invention, the label may be any substance which generates a detectable signal when released upon lysis of the liposome. In one liposome embodiment of the invention, the label is a signal enzyme, as described above, which, when released by lysis of the liposome, converts a substrate to a signal generating product. In the preferred liposome embodiment of the invention, the label may be a dye which may be distinguished from dye remaining in unlysed liposomes by known techniques such as fluorescence polarization or fluorescence quenching.

Lysis of the liposome may be accomplished by any conventional agent. Suitable agents are cytolysins, such as melittin, various viral fusion proteins, and, most preferably, complement. Complement selectively lyses liposomes having a bound fraction conjugated thereto in the presence of liposomes lacking a bound fraction whereby the second binding reaction may be performed in homogeneous mode.

It is evident that signal amplification occurs in any embodiment of the invention, irrespective of the assay configuration, because each of the enzymes acts as a true catalyst wherein a single molecule may act on an essentially unlimited number of masked ligand or substrate molecules without being consumed. Thus, in theory, one molecule of each enzyme would be sufficient to perform the method of the invention. In practice, determination of the amounts of enzyme to be added are well within the purview of one of ordinary skill in the art.

As described heretofore, the method of the invention is a two stage amplification. If additional signal amplification is desired, a multistage cascade amplification assay may be carried out. For example, the unmasking enzyme, instead of acting directly on the masked ligand, may serve as a first enzyme which enzymatically converts a reagent in the assay medium to a second enzyme which performs the unmasking. Alternatively, the first enzyme, or any subsequent enzyme, may also react with additional reagents to provide additional enzymes which may continue the cascade of enzymatic reactions until the masking ligand is unmasked. By proper selection of reagents to be added to the assay medium, any desired number of amplification stages may be carried out.

Another aspect of the invention is a reagent kit or package of materials for performing an assay for an analyte in accordance with the method of the invention. The kit may include an antianalyte affixed to a solid support, a tracer comprising an unmasking enzyme conjugated to the analyte or a second antianalyte, a masked ligand optionally conjugated to a signal enzyme and an antiligand optionally affixed to the solid support and optionally conjugated to the signal enzyme. The kit may also include a liposome which encapsulates a label and which is conjugated to the ligand, a standard for the analyte, as, for example, one or more analyte samples of known concentration, or it may include other reagents, such as an enzyme substrate, buffer or saline useful in carrying out the assay. The components of the kit may be supplied in separate containers, as, for example, vials, or two or more of the components may be combined in a single container.

The method of the invention includes several steps which are conventional in the EIA art. For example, conjugation of enzymes to ligands and antiligands, affixation of assay components to a solid support, preparation and lysis of label-loaded, ligand-conjugated liposomes, and modification of ligands by covalent conjugation of functional groups are all well-known to those skilled in the art and no further details with respect to these method steps and assay components are deemed necessary for a complete understanding of the invention.

The following examples are provided to further describe the invention:

EXAMPLE I

CASCADE ASSAY FOR ADENOVIRUS (Assay configuration of FIG. 3)

Preparation of antibodies

Antiserum against fluorescein was raised in rabbits by immunization with a fluorescein isothiocyanate-bovine serum albumin conjugate by techniques well-known in the art.

Monoclonal antibodies against adenovirus were produced by conventional techniques, and originated from Balb/c mice immunized with purified hexon protein.

Preparation of antibody-porcine liver carboxy esterase conjugate

Commercially available porcine liver esterase (PLE) (Sigma Chemical Co.) was exhaustively dialyzed against phosphate buffered normal saline solution, pH 7.6. This material was coupled to an anti-adenovirus monoclonal antibody using the "two-step" glutaraldehyde method: PLE, 2.0 mg, in 800 uL of 50 mM phosphate, pH 7.2 was activated with 0.16% glutaraldehyde for 50 minutes at 20° C. To this was added 1.6 mg of antibody, also in 50 mM phosphate buffer to give a final volume of 1.06 mL. After a 75 minute incubation at room temperature, the conjugate was isolated by size exclusion chromatography.

Construction of the immunological sandwich with unmasking enzyme.

A polyvinylchloride microtiter plate was coated for 15 hours at 4° C. with 100 uL/well of a 10 mM sodium bicarbonate (pH 9.5) solution containing the following:
(1) (mouse) anti-adenovirus monoclonal antibody at 11 ug/mL.
(2) (rabbit) anti-fluorescein polyclonal antibody (IgG fraction) at 0.34 ug/mL.

Following incubation, the coating solution was removed, and a sonicated suspension of adenovirus infected HeLa cells (antigen) was titered across the plate in two-fold serial dilutions. The diluent for the antigen was composed of 10 mM tris (hydroxymethyl) aminomethane (TRIS), 150 mM saline, 2% casein (w/v), 0.05% polyoxyethylenesorbitan monolaurate (TWEEN-20) at pH 7.6. Antigen was incubated at 37° C. for one hour. The plate was washed once with the TRIS-casein solution without detergent (200 uL/well). Anti-adenovirus antibody-porcine liver esterase conjugate was added to each well (100 uL) at an approximate concentration of 20 ug/mL. Again, the plate was incubated at 37° C. for one hour, and washed three times with 200 uL/well of TRIS-casein.

Generation of unmasked ligand and second binding reaction

To each well was added 100 uL of a solution containing $10^{-8}$M fluorescein dibutyrate (Pfaltz & Bauer, Inc.) in 50 mM phosphate, pH 7.5. The plate was incubated at 37° C. for one hour, and subsequently washed three times with 2000 uL/well of TRIS-casein buffer.

Competition with signal enzyme-ligand conjugate, and signal detection

Figure 8:
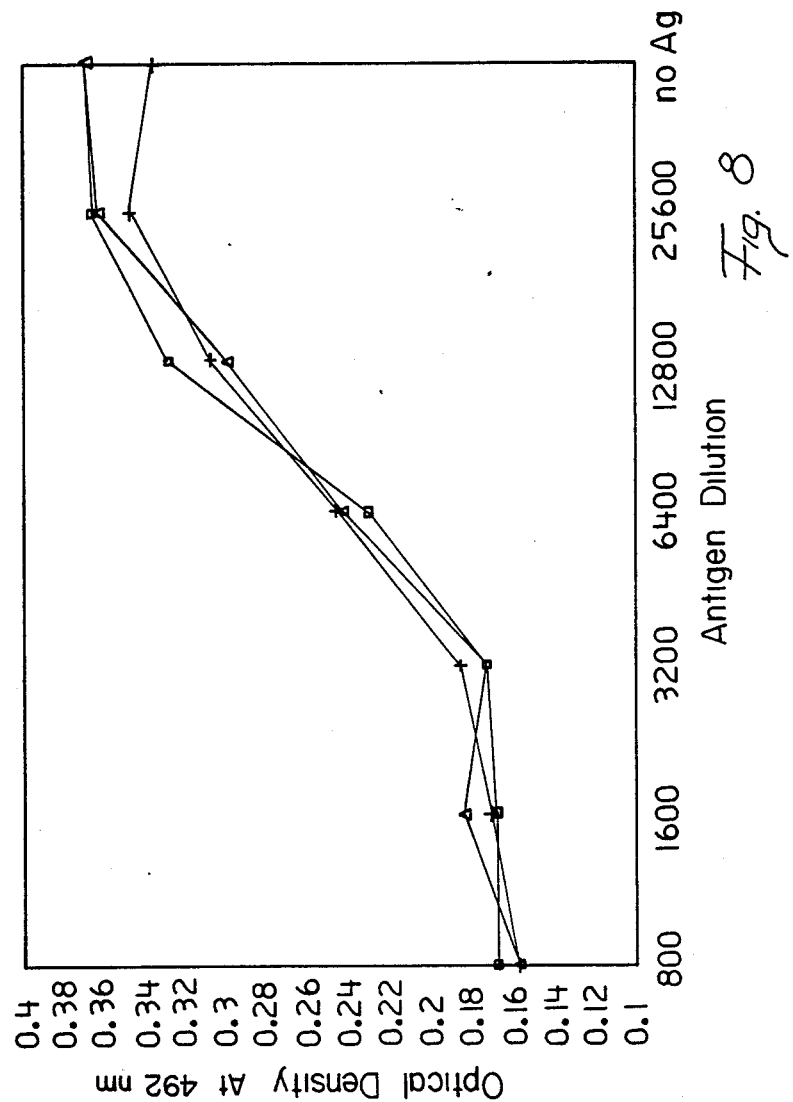
FIG. 8 shows the results of a typical assay carried out by the method of the invention.

To each well was added 100 uL of a solution containing fluorescein-horseradish peroxidase conjugate (Sigma Chemical Co.) at a concentration of 0.002 ug/mL in TRIS-casein. Following a one hour incubation at 37° C., the plate was again washed three times with TRIS- casein, and once with 0.1 M sodium citrate, pH 5.0. A chromogenic solution containing 3.62 mg/mL of o-phenylenediamine, and 0.68 uL/mL of 30% hydrogen peroxide in 0.1 M sodium citrate at pH 5.0. Color development was arrested after five minutes by the addition of 100 uL/well of 4.5 N sulfuric acid. Resulting optical densities were subsequently determined at 492 nm. The results of triplicate runs are shown in FIG. 8.

EXAMPLE II

Cascade Assay For HSV (Assay configuration of FIG. 5)

The wells of a polyvinylhloride microtiter plate are coated with anti HSV antibody (AA), unfilled binding sites of the plate are blocked with casein, and the wells are incubated with a test sample suspected of containing HSV (A). After decantation, the wells are incubated with a solution of anti HSV antibody conjugated to alkaline phosphatase, (T-Eu), the solution is decanted from the wells, and the wells are washed thoroughly. To each well is added solutions of 4-acetamidophenyl phosphate (ML) and rabbit antiacetaminophen antibody (AL). The plate is incubated, and each well is treated with adipaminophen conjugated to malate dehydrogenase (L-Es), and incubated again. Each well is then treated with a mixture of oxalacetate and nicotinamide adenine dinucleotide reduced form (NADH), (S). The enzymatic activity of malate dehydrogenase is inhibited by the binding of L-Es to AL, and is monitored by the decrease in NADH concentration, measured spectrophotometrically at 340 nm.

EXAMPLE III

Cascade Assay For HSV (Assay configuration of FIG. 6)

This example is the same as Example II except the adipaminophen-malate dehydrogenase conjugate is replaced by adipaminophen conjugated liposomes loaded with a dye or an enzyme. Following the final incubation, an appropriately titered guinea pig complement solution is added to the wells to induce lysis of those liposomes having a bound fraction on their surfaces. Released dye is then detected by conventional fluorescence or released enzyme is detected by addition of an enzyme substrate.

Thus, the invention provides an EIA method including two or more binding reactions. A first binding reaction between analyte, antianalyte and tracer provides an unmasking enzyme on a solid support. The enzyme unmasks a masked ligand to give a free ligand which binds with an antiligand in a second binding reaction. The second binding activates a signal system which includes a signal enzyme or complement to provide an amplified signal which is proportional to the concentration of the analyte.

What is claimed is:

1. A method for determining an analyte in a liquid comprising:
    (a) combining a first liquid suspected of containing an analyte with a tracer comprising an unmasking enzyme and with a solid support having an antianalyte and a first immunologically active component randomly affixed thereto whereby said analyte binds to said antianalyte and said tracer binds to one of said analyte and said antianalyte to give a first bound fraction on said support;
    (b) replacing said first liquid with a second liquid containing a second immunologically active compound conjugated to a masking group, said unmasking enzyme removing said masking group to give free second component which binds to said first component, and a signal enzyme conjugated to one of said second component and a third immunologically active component specific for said second component, said signal enzyme becoming affixed to said support;
    (c) replacing said second liquid with a third liquid containing a substrate which converted by said signal enzyme to a product; and
    (d) determining said analyte by a signal associated with said product.

2. The method in accordance with claim 1 wherein said tracer binds to said antianalyte and further comprises said analyte having said enzyme conjugated thereto.

3. The method in accordance with claim 1 wherein said tracer binds to said analyte and further comprises a second antianalyte having said enzyme conjugated thereto.

4. The method in accordance with claim 1 wherein said solid support further comprises an inert protein which fills binding sites of the support unoccupied by antianalyte and antiligand.

5. The method in accordance with claim 1 wherein said analyte is selected from the group consisting of an antigen, an antibody and a hapten.

6. The method in accordance with claim 1 wherein said antianalyte is selected from the group consisting of an antigen, and an antibody.

7. The method in accordance with claim 1 wherein said second component is a ligand of molecular weight not greater than 2,000.

8. The method in accordance with claim 7 wherein said ligand has a molecular weight of from about 200 to 1000.

9. The method in accordance with claim 8 wherein said ligand is selected from the group consisting of a steroid, vitamin, drug, hormone and coenzyme.

10. The method in accordance with claim 9 wherein said ligand is selected from the group consisting of a steroid, folate, thyroxine, vitamin $B_{12}$, riboflavin, biotin, pepstatin and cyclic adenosine monophosphate.

11. The method in accordance with claim 1 wherein said masking group is selected from the group consisting of a phosphate group, an acyl group, a carboxamide group, a peptide group and an isomerable double bond.

12. The method in accordance with claim 1 wherein said unmasking enzyme is selected from the group consisting of a hydrolase, cyclase and isomerase.

13. The method in accordance with claim 12 wherein said hydrolase is selected from the group consisting of a protease, esterase and phosphatase.

14. The method in accordance with claim 1 wherein said signal enzyme is encapsulated in a vesicle and further comprises vesicle lysing means in said third liquid.

15. The method in accordance with claim 14 wherein said vesicle lysing means is a reagent selected from the group consisting of complement, melittin and a viral fusion protein.

16. The method in accordance with claim 1 wherein said signal is a color associated with said substrate.

17. The method in accordance with claim 1 wherein said signal is a color associated with said product.

18. The method of accordance with claim 1 wherein said first component is an antiligand and said second component is a ligand conjugated to said signal enyzme.

19. The method in accordance with claim 1 wherein said first component is a ligand, said second component is said ligand and said signal enzyme is conjugated to an antiligand.

20. The method in accordance with claim 1 wherein said first component is an antiligand, said second component is a ligand and said signal enzyme is conjugated to an increment of said ligand which is not conjugated to said masking group.

21. The method in accordance with claim 1 wherein said first component is a first antiligand, said second component is a ligand and said signal enzyme is conjugated to a second antiligand.

22. A method for determining an analyte in a liquid comprising:
(a) combining a first liquid suspected of containing an analyte with a tracer comprising an unmasking enzyme and with a solid support having an antianalyte and an antiligand randomly affixed thereto whereby said analyte binds to said antianalyte and said tracer binds to said analyte to give a bound fraction on said support;
(b) separating said support from said first liquid;
(c) suspending said support in a second liquid;
(d) adding to said second liquid a ligand conjugated to a masking group and a liposome having ligand conjugated thereto and having a signal enzyme encapsulated therein, said unmasking enzyme removing said masking group to give free ligand, said antiligand binding competitively with said ligand on said liposome and said free ligand;
(e) adding complement and a substrate for signal enzyme to said second liquid, said complement lysing a liposome having conjugated thereto ligand bound to antiligand, said lysing causing release of said signal enzyme, the released signal enzyme converting said substrate to a product; and
(f) determining said analyte by a signal associated with said product.

23. The method in accordance with claim 22 wherein said label is selected from the group consisting of a dye and a signal enzyme.

24. The method in accordance with claim 23, further comprising adding a substrate to said second liquid, said substrate reacting with said signal enzyme to give a product wherein said signal is color associated with one of said substrate and product.

25. The method in accordance with claim 22 further comprising subjecting said second liquid to excitation light wherein said signal is associated with fluorescence emission from said dye.

26. A method for determining an antigen in a fluid comprising:
(a) combining a first liquid suspected of containing a antigen with a first antibody conjugated to an unmasking enzyme and a solid support having randomly affixed thereto an antiligand and a second antibody whereby said first and second antibodies bind to said antigen to give a first bound fraction on said support;
(b) separating said support from said first liquid;
(c) suspending said support in a second liquid;
(d) adding to said second liquid a first increment of a ligand conjugated to a signal enzyme and a second increment of said ligand conjugated to a masking group, said unmasking enzyme converting the masked ligand to free ligand, said free ligand and said first increment of ligand binding competitively with said antiligand on said support;
(e) separating said support from said second liquid;
(f) suspending said support in a third liquid;
(g) adding to said third liquid a substrate for said signal enzyme whereby said signal enzyme converts said substrate to a product; and
(h) determining said antigen by a signal associated with said product.

27. A method for determining an antigen in a fluid comprising:
(a) combining a first liquid suspected of containing an antigen with a first antibody conjugated to an unmasking enzyme and a solid support having randomly affixed thereto a first antiligand and a second antibody whereby said first and second antibodies bind to said antigen to give a first bound fraction on said support;
(b) separating said support from said first liquid;
(c) suspending said support in a second liquid;

(d) adding to said second liquid a masked ligand and a second antiligand conjugated to a signal enzyme, said unmasking enzyme converting said masked ligand to a free ligand, said free ligand binding to said first and second antiligands whereby said signal enzyme becomes affixed to said support;

(e) separating said support from said second liquid;

(f) suspending said support in a third liquid;

(g) adding to said third liquid a substrate for said signal enzyme whereby said signal enzyme converts said substrate to a product; and (h) determining said antigen by a signal associated with said product.

28. A kit of materials for performing an assay for an analyte comprising a solid support having randomly affixed thereto an antianalyte and an immunologically active compound, a tracer comprising an unmasking enzyme conjugated to an analyte, a masked ligand and a signal enzyme.

29. The kit in accordance with claim 28 wherein said signal enzyme is conjugated to one of said masked ligand and an antiligand.

30. The kit in accordance with claim 29 further comprising a sac having said signal enzyme encapsulated therein and a second immunologically active compound conjugated thereto.

31. The kit in accordance with claim 28 further comprising at least one other reagent selected from the group consisting of complement, an enzyme substrate, buffer, saline, a liquid containing analyte of known concentration and a liquid substantially free of analyte.

* * * * *